US006403768B1

(12) United States Patent
Simmons et al.

(10) Patent No.: US 6,403,768 B1
(45) Date of Patent: Jun. 11, 2002

(54) MANIPULATION OF MLO GENES TO ENHANCE DISEASE RESISTANCE IN PLANTS

(75) Inventors: Carl R. Simmons, Des Moines, IA (US); Guo-Hua Mia, Hockessin, DE (US)

(73) Assignees: Pioneer Hi-Bred International, Inc., Des Moines, IA (US); E.I. Du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/558,679

(22) Filed: Apr. 26, 2000

Related U.S. Application Data

(62) Division of application No. 09/350,268, filed on Jul. 6, 1999, now Pat. No. 6,211,433.
(60) Provisional application No. 60/091,875, filed on Jul. 7, 1998.

(51) Int. Cl.[7] ........................ A61K 35/78; C07K 14/00
(52) U.S. Cl. ........................................ 530/370; 530/350
(58) Field of Search ................................. 530/350, 370

(56) References Cited

U.S. PATENT DOCUMENTS 5,629,470 A 5/1997 Lam et al. .................. 800/205

FOREIGN PATENT DOCUMENTS

WO WO 98/04586 2/1998
WO WO 99/23235 5/1999

OTHER PUBLICATIONS

Bennetzen et al., Approaches and Progress in the Molecular Cloning of Plant Disease Resistance Genes, 1992, *Genetic Engineering,* vol. 14, pp. 99–124.

Blewitt et al., ESTs from Developing Cotton Fiber, Jun. 12, 1999, Database EMBL Sequence Database Online, AC/ID AI729043, Abstract XP002119430.

Blewitt et al., ESTs from Developing Cotton Fiber, Jun. 12, 1999, Database EMBL Sequence Database Online, AC/ID AI731933, Abstract XP002119432.

Buschges et al., The Barley Mio Gene: A Novel Control Element of Plant Pathogen Resistance, *Cell,* Mar. 7, 1997, pp. 695–705, vol. 88, Cell Press.

Covitz et al., Expressed Sequence Tags from a Root Hair–Enriched Medicago Trunculata cDNA Library, Nov. 14, 1997, Database EMEST2 Online, AC/ID AA660856, Abstract XP002119426.

Linthorst et al., Constitutive Expression of Pathogenesis––Related Proteins PR–1, GRP, and PR–5in Tobacco Has No Effect on Virus Infection, Mar. 1989, *The Plant Cell,* vol. 1, pp. 285–291.

Nemoto, Y., Isolation of Novel Early Salt–Responding Genes from Wheat (*Triticum Aestivum L.*) by Differential Display, Jul. 4, 1999, Database EMBL Sequence Database Online, AC/ID AB011444, Abstract XP002119431.

Walbot, V., Maize ESTs from Various cDNA Libraries Sequenced at Stanford University, Apr. 26, 1999, Database EMEST11 Online, AC/ID AI621523, Abstract XP002119428.

Walbot, V., Maize ESTs from Various Cdna Libraries sequenced at Stanford University, May 1, 1999, Database EMEST12 Online, AC/ID ai649550, Abstract XP002119429.

Walbot, V., Maize ESTs from Various cDNA Libraries Sequenced at Stanford University, May 17, 1999, Database EMEST12 Online, AC/ID AI668283, Abstract XP002119427.

*Primary Examiner*—Karen Cochrane Carlson
(74) *Attorney, Agent, or Firm*—Alston & Bird LLP

(57) ABSTRACT

Compositions and methods for enhancing disease resistance in plants are provided. The method involves modulating the activity of the Mlo3 sequences in the plant. Mlo3 sequences are provided that can be manipulated to enhance pathogen resistance in modified plants. Transformed plants, plant cells, tissues, and seed are also provided having enhanced disease resistance.

5 Claims, 2 Drawing Sheets

FIG. 1.

```
CLUSTAL W (1.74) multiple sequence alignment

ZmMLO3_         ------MSEEATLEDTPTWIVASVCSVIVLISFVFERALHHLGKALERRR-KTLYEALLK
HvMLO1_         -MSDKKGVPARELPETPSWAVAVVFAAMVLVSVLMEHGLHKLGHWFQHRHKKALWEALEK

ZmMLO3_         LKEELMLLGFVSLLLVVSQD-LIQKICIDDS-LMEHWMPCRGASATASAHYGVSSSSSSS
HvMLO1_         MKAELMLVGFISLLLIVTQDPIIAKICISED-AADVMWPCKRGTEGRKPS----------

ZmMLO3_         AVGGGRR----------------MLKGGG------------------AAFGHCSSKGKVP
HvMLO1_         ------------------------------------------K------YVDYCPEGKVA

ZmMLO3_         LLSLHALEQVHIFIFVLAITQVVLSVATVLLGLLQMRIWMHWENTIQQEGSSAPKMIAR-
HvMLO1_         LMSTGSLHQLHVFIFVLAVFHVTYSVITIALSRLKMRTWKKWETETTSLEYQFANDPARF

ZmMLO3_         -------------VQKIRFIQDRCKGYEKAAWVIIWLRSFFKQFYGSVSNDDYIAMRLGF
HvMLO1_         R-----------FTHQTSFVKRHL--GLSSTPGIRWVVAFFRQFFRSVTKVDYLTLRAGF

ZmMLO3_         VMEHFRGHPKFNFYDYMIKALEKDRKRVVSIKWYYWIFVMIFLLLNVTGWHSYFWISLVP
HvMLO1_         INAHLSQNSKFDFHKYIKRSMEDDFKVVVGISLPLWGVAILTLFLDINGVGTLIWISFIP

ZmMLO3_         LALLLLIGTKLEHIINRLAYEVASKHAAGQGEGGIVVSPSDELFWFRSPRLVLVLIHFIL
HvMLO1_         LVILLCVGTKLEMIIMEMALEIQDRAS--VIKGAPVVEPSNKFFWFHRPDWVLFFIHLTL

ZmMLO3_         FQNAFEFAYFFWTLAMFGANSCIMDSLGYSVSRIIICVVVQVLCSYSTLPLYAIVSHMGS
HvMLO1_         FQNAFQMAHFVWTVATPGLKKCYHTQIGLSIMKVVVGLALQFLCSYMTFPLYALVTQMGS

ZmMLO3_         SFKSAVFVDDVADNLRGWADGARRRVRRSA--TG-----VDASC---LGTPAAAGRGWEG
HvMLO1_         NMKRSIFDEQTSKALTNWRNTAKEKKKVRD---TDMLMAQMIG----DATPSRGSSPMPS

ZmMLO3_         AAGWRLIAGRPS----------RPTQQPRSISF---------------------------
HvMLO1_         RGSSPVHLLHKGM-------GRSDDPQSAPTSPR---T------QQEARDMYPVVVAHPV

ZmMLO3_         ------------------------------------------
HvMLO1_         HRLNPNDRRRSASSSALEADIPSADFSFSQG-----------
```

MANIPULATION OF MLO GENES TO ENHANCE DISEASE RESISTANCE IN PLANTS

CROSS-REFERENCE

This application is a divisional of U.S. application Ser. No. 09/350,268, filed Jul. 6, 1999, now U.S. Pat. No. 6,211,433, which claims the benefit of U.S. Provisional Application No. 60/091,875, filed Jul. 7, 1998.

FIELD OF THE INVENTION

The invention relates to the genetic manipulation of plants, particularly to transforming plants with genes that enhance disease resistance.

BACKGROUND OF THE INVENTION

Disease in plants is caused by biotic and abiotic causes. Biotic causes include fingi, viruses, bacteria, and nematodes. Of these, fungi are the most frequent causative agent of disease on plants. Abiotic causes of disease in plants include extremes of temperature, water, oxygen, soil pH, plus nutrient-element deficiencies and imbalances, excess heavy metals, and air pollution.

A host of cellular processes enables plants to defend themselves from disease caused by pathogenic agents. These processes apparently form an integrated set of resistance mechanisms that is activated by initial infection and then limits further spread of the invading pathogenic microorganism. This limitation of the pathogen intruder is frequently accomplished by localized containment of the intruder following a coordinated complex defense response.

Subsequent to recognition of a potentially pathogenic microbe, plants can activate an array of biochemical responses. Generally, the plant responds by inducing several local responses in the cells immediately surrounding the infection site. The most common resistance response observed in both nonhost and race-specific interactions is termed the "hypersensitive response" (HR). In the hypersensitive response, cells contacted by the pathogen, and often neighboring cells, rapidly collapse and dry in a necrotic fleck. Other responses include the deposition of callose, the physical thickening of cell walls by lignification, and the synthesis of various antibiotic small molecules and proteins. Genetic factors in both the host and the pathogen determine the specificity of these local responses, which can be very effective in limiting the spread of infection.

The hypersensitive response in many plant-pathogen interactions is specified by and dependent on the presence of two complementary genes, one from the host and one from the pathogen. These complementary genes are the resistance (R) gene in the plant and a corresponding avirulence (avr) gene in the pathogen. The interaction of the genes is associated with the rapid, localized cell death of the hypersensitive response. R genes that respond to specific bacterial, fungal, or viral pathogens, have been isolated from a variety of plant species and several appear to encode cytoplasmic proteins.

The resistance gene in the plant and the avirulence gene in the pathogen often conform to a gene-for-gene relationship. That is, resistance to a pathogen is only observed when the pathogen carries a specific avirulence gene and the plant carries a corresponding or complementing resistance gene. Because avr-R gene-for-gene relationships are observed in many plant-pathogen systems and are accompanied by a characteristic set of defense responses, a common molecular mechanism underlying avr-R gene mediated resistance has been postulated. A simple model which has been proposed is that pathogen avr genes directly or indirectly generate a specific molecular signal (ligand) that is recognized by cognate receptors encoded by plant R genes.

Both plant resistance genes and corresponding pathogen avirulence genes have been cloned. The plant kingdom contains thousands of R genes with specific specificities for viral, bacterial, fungal, or nematode pathogens. Although there are differences in the defense responses induced during different plant-pathogen interactions, some common themes are apparent among R gene-mediated defenses. The function of a given R gene is dependent on the genotype of the pathogen. Plant pathogens produce a diversity of potential signals, and in a fashion analogous to the production of antigens by mammalian pathogens, some of these signals are detectable by some plants.

The avirulence gene causes the pathogen to produce a signal that triggers a strong defense response in a plant with the appropriate R gene. However, expressing an avirulence gene does not stop the pathogen from being virulent on hosts that lack the corresponding R gene. A single plant can have many R genes, and a pathogen can have many avr genes.

Monogenic resistance mediated by recessive (mlo) alleles of the Mlo locus is different. It differs from race-specific incompatibility to single pathogen strains in that it is believed to confer a broad spectrum resistance to almost all known isolates of the fungal pathogen, and the resistance is apparently durable in the field despite extensive cultivation. Further, mlo resistance alleles have been obtained by mutagen treatment of susceptible wild-type Mlo varieties. These mlo plants exhibit a spontaneous leaf cell death phenotype under pathogen-free or even axenic conditions.

As noted, among the causative agents of infectious disease of crop plants, the phytopathogenic fungi play the dominant role. Phytopathogenic fungi cause devastating epidemics, as well as causing significant annual crop yield losses. All of the approximately 300,000 species of flowering plants are attacked by pathogenic fungi. However, a single plant species can be host to only a few fungal species, and similarly, most fungi usually have a limited host range.

Plant disease outbreaks have resulted in catastrophic crop failures that have triggered famines and caused major social change. Generally, the best strategy for plant disease control is to use resistant cultivars selected or developed by plant breeders for this purpose. However, the potential for serious crop disease epidemics persists today, as evidenced by outbreaks of the Victoria blight of oats and southern corn leaf blight.

Accordingly, molecular methods are needed to supplement traditional breeding methods to protect plants from pathogen attack. Particularly, methods are needed for broad spectrum resistance to pathogens.

SUMMARY OF THE INVENTION

Compositions and methods for creating or enhancing resistance to plant pests are provided. The method provides control of pathogens by modulating the expression of the Mlo3 gene. A novel Mlo sequence is provided from maize. This sequence can be utilized to modulate the expression of the Mlo3 gene in plants, particularly maize, to enhance resistance to pathogens. Generally, such modulation will result in decreased or increased expression of the native Mlo3 gene, preferably decreased expression. Such decreased expression can be effected by mutagenesis or expression of modified or antisense Mlo3 sequences described herein.

It is recognized that a variety of promoters will be useful in the invention, the choice of which will depend in part upon the desired level of expression of the modified sequence in the plant or alternatively, in the plant organ. It is recognized that the levels of expression can be controlled to induce broad spectrum resistance resulting in levels of immunity in the plant or to induce cell death.

The methods of the invention find use in controlling plant pests, including fungal pathogens, viruses, nematodes, insects, and the like. Transformed plants and seeds, as well as methods for making such plants and seeds are additionally provided.

BRIEF DESCRIPTION OF THE DRAWINGS

FIG. 1 provides a sequence alignment for the maize Mlo3 homologue with the barley Mlo sequence. The barley sequence is designated as HvMlo1.

DETAILED DESCRIPTION OF THE INVENTION

Figure 2:
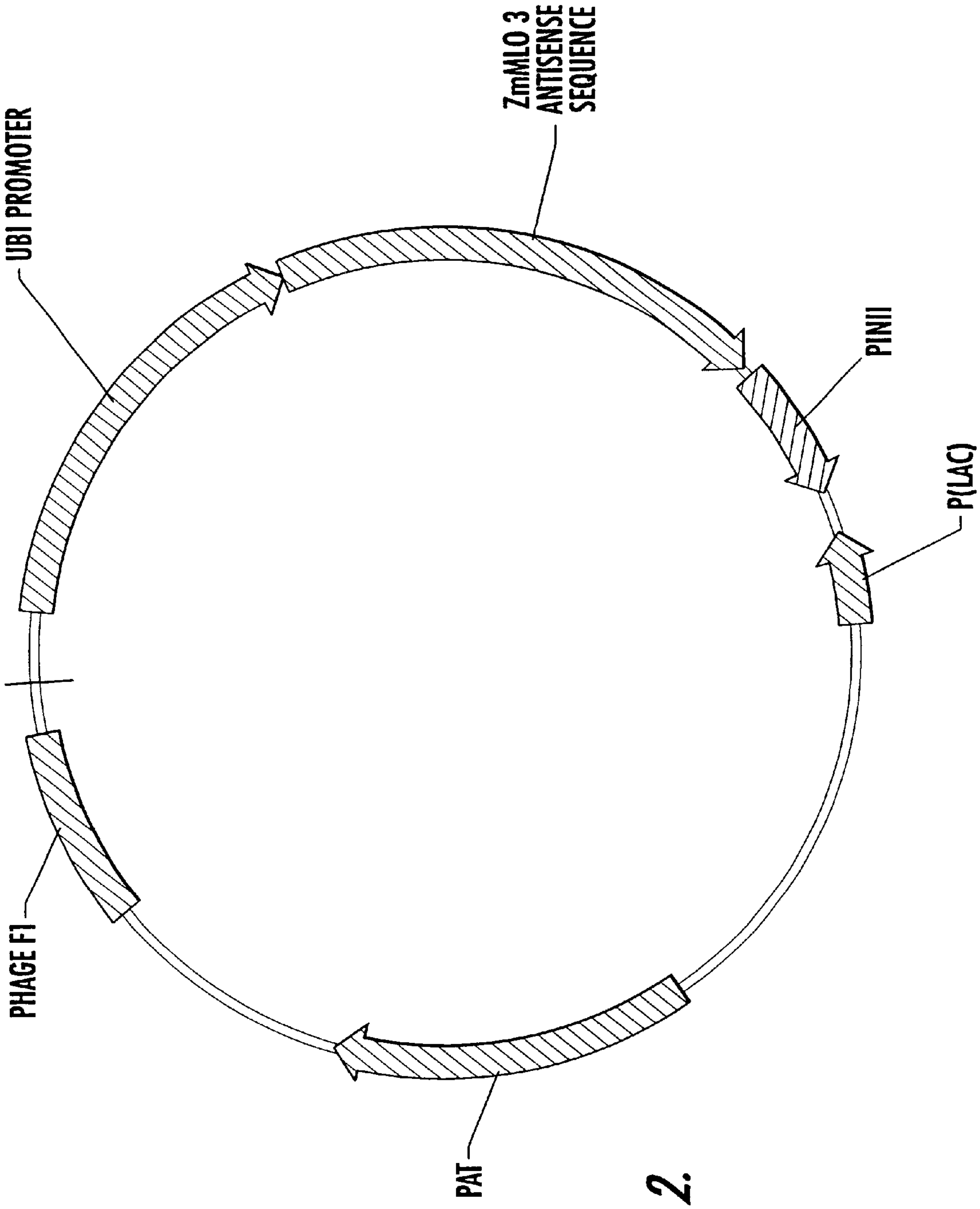
FIG. 2 schematically illustrates a plasmid vector comprising the ZmMlo3 antisense construct operably linked to the ubiquition promoter.

Compositions of the invention include a mutation-induced recessive allele of maize Mlo3 set forth in SEQ ID NO: 1. The maize sequence exhibit homology to the Mlo barley sequence (SEQ ID NO: 3). See, Büschges et al. (1997) 88:695–705. The isolated maize Mlo3 gene is involved in enhancing resistance to plant pests. In particular, the present invention provides for an isolated nucleic acid molecule comprising nucleotide sequences encoding the amino acid sequence shown in SEQ ID NO: 2. Further provided are polypeptides having an amino acid sequence encoded by the nucleic acid molecule described herein as SEQ ID NO:1 and fragments and variants thereof The invention encompasses isolated or substantially purified nucleic acid or protein compositions. An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein having less than about 300/, 20%, 10%, 5%, (by dry weight) of contaminating protein. When the protein of the invention or biologically active portion thereof is recombinantly produced, preferably culture medium represents less than about 30%, 20%, 10%, or 5% (by dry weight) of chemical precursors or non-protein-of-interest chemicals.

Fragments and variants of the disclosed nucleotide sequence and protein encoded thereby are also encompassed by the present invention. By "fragment" is intended a portion of the nucleotide sequence or a portion of the amino acid sequence and hence protein encoded thereby. Fragments of a nucleotide sequence may encode protein fragments that retain the biological activity of the native protein and hence their altered expression enhances resistance to pathogens. Alternatively, fragments of a nucleotide sequence that are useful as hybridization probes generally do not encode fragment proteins retaining biological activity. Thus, fragments of a nucleotide sequence may range from at least about 20 nucleotides, about 50 nucleotides, about 100 nucleotides, and up to the full-length nucleotide sequence encoding the proteins of the invention.

A fragment of the Mlo3 nucleotide sequence that encodes a biologically active portion of the Mlo3 protein of the invention will encode at least 15, 20, 25, 30, 40, 50, 75, 100, 200, 250, 300, 350, 400, 450 contiguous amino acids, or up to the total number of amino acids present in the full-length MLO3 protein of the invention. Fragments of the Mlo3 nucleotide sequence that are useful as hybridization probes for PCR primers generally need not encode a biologically active portion of the MLO3 protein.

Thus, a fragment of the Mlo3 nucleotide sequence may encode a biologically active portion of the MLO3 protein, or it may be a fragment that can be used as a hybridization probe or PCR primer using methods disclosed below. A biologically active portion of the MLO3 protein can be prepared by isolating a portion of the Mlo3 nucleotide sequences of the invention, expressing the encoded portion of the MLO3 protein (e.g., by recombinant expression in vitro), and assessing the activity of the encoded portion of the MLO3 protein. Nucleic acid molecules that are fragments of the Mlo3 nucleotide sequence comprise at least 15, 20, 50, 75, 100, 150, 200, 250, 300, 350, 400, 450, 500, 550, 600, 650, 700, 800, 900, 1,000, 1,100, 1,200, 1,300, 1,400, 1,500, 1,600, 1,700, 1,800 nucleotides, or up to the number of nucleotides present in the full-length Mlo3 nucleotide sequence disclosed herein.

By "variants" is intended substantially similar sequences. For nucleotide sequences, conservative variants include those sequences that, because of the degeneracy of the genetic code, encode the amino acid sequence of the MLO3 polypeptide of the invention. Naturally occurring allelic variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis but which still encode the MLO3 protein of the invention. Generally, nucleotide sequence variants of the invention will have at least 40%, 50%, 60%, 70%, generally, 80%, preferably 85%, 90%, up to 95%, 98% sequence identity to its respective native nucleotide sequence.

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may result from, for example, genetic polymorphism or from human manipulation.

The protein of the invention may be altered in various ways including amino acid substitutions, deletions, truncations, and insertions. Methods for such manipulations are generally known in the art. For example, amino acid sequence variants of the MLO3 protein can be prepared by mutations in the DNA. Methods for mutagenesis and nucleotide sequence alterations are well known in the art. See, for example, Kunkel (1985) *Proc. Natl. Acad. Sci. USA*

82:488–492; Kunkel et al. (1987) *Methods in Enzymol.* 154:367–382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferred.

Thus, the gene and the nucleotide sequence of the invention include both the naturally occurring sequence as well as mutant forms. Likewise, the protein of the invention encompasses both naturally occurring proteins as well as variations and modified forms thereof. Such variants will continue to possess the desired ability to enhance resistance to pathogens when their expression is altered. Obviously, the mutations that will be made in the DNA encoding the variant must not place the sequence out of reading frame and preferably will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by an enhanced resistance to pathogens when the expression of the protein sequences is altered.

Variant nucleotide sequences and proteins also encompass sequences and proteins derived from a mutagenic and recombinogenic procedure such as DNA shuffling. With such a procedure, one or more different Mlo3 coding sequences can be manipulated to create a new Mlo3 coding sequence possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the Mlo3 gene of the invention and other known genes involved in pathogen resistance to obtain a new gene coding for a protein with an improved property of interest, such as an increased $K_m$ in the case of an enzyme. Strategies for such DNA shuffling are known in the art. See, for example, Stemmer (1994) *Proc. Natl. Acad. Sci. USA* 91:10747–10751; Stemmer (1994) *Nature* 370:389–391; Crameri et al. (1997) *Nature Biotech.* 15:436–438; Moore et al. (1997) *J. Mol. Biol.* 272:336–347; Zhang et al. (1997) *Proc. Natl. Acad. Sci. USA* 94:4504–4509; Crameri et al. (1998) *Nature* 391:288–291; and U.S. Pat. Nos. 5,605,793 and 5,837,458.

The maize Mlo3 homologue is associated with disease related loci as shown in Table 1. Mapping information of the sequence is given in Table 3. The maize sequences find use in negative control function of the MLO3 protein in leaf cell death and in the onset of pathogen defense. Generally, the methods of the invention take advantage of the absence of MLO3 to prime responsiveness of the plant to disease.

The nucleotide sequences of the invention can be used to isolate corresponding sequences from other organisms, particularly other plants, more particularly other monocots. In this manner, methods such as PCR, hybridization, and the like can be used to identify such sequences based on their sequence homology to the sequences set forth herein. Sequences isolated based on their sequence identity to the entire Mlo3 sequences set forth herein or to fragments thereof are encompassed by the present invention.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds, (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the Mlo sequences of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, New York).

For example, the entire sequence of the Mlo3 nucleotide sequences disclosed herein, or one or more portions thereof, may be used as a probe capable of specifically hybridizing to corresponding Mlo3 sequences and messenger RNAs. To achieve specific hybridization under a variety of conditions, such probes include sequences that are unique among Mlo3 sequences and are preferably at least about 10 nucleotides in length, and most preferably at least about 20 nucleotides in length. Such probes may be used to amplify corresponding Mlo3 sequences from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267–284: $T_m$=81.5° C.+16.6 (log M)+0.41 (%GC)−0.61 (% form)−500/L; where M is the molarity of monovalent cations, %GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes,* Part I, Chapter 2 (Elsevier, N.Y.); and Ausubel et al., eds. (1995) *Current Protocols in Molecular Biology,* Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

In general, a sequence that encodes a Mlo3 protein and hybridize to the Mlo sequences disclosed herein will be at least 40% to 50% homologous, about 60% to 70% homologous, and even about 80%, 85%, 90%, 95% to 98% homologous or more with the disclosed sequences. That is, the sequence similarity of sequences may range, sharing at least about 40% to 50%, about 60% to 70%, and even about 80%, 85%, 90%, 95% to 98% sequence similarity.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Optimal alignment of sequences for comparison may be conducted by the local homology algorithm of Smith et al. (1981) *Adv. Appl. Math.* 2:482; by the homology alignment algorithm of Needleman et al. (1970) *J. Mol. Biol.* 48:443; by the search for similarity method of Pearson et al. (1988) *Proc. Natl. Acad. Sci.* 85:2444; by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Drive, Madison, Wis., USA; the CLUSTAL program is well described by Higgins et al. (1988) *Gene* 73:237–244 (1988); Higgins et al. (1989) *CABIOS* 5:151–153; Corpet et al. (1988) *Nucleic Acids Res.* 16:10881–90; Huang et al. (1992) *Computer Applications in the Biosciences* 8:155–65, and Person et al. (1994) *Meth. Mol. Biol.* 24:307–331; preferred computer alignment methods also include the BLASTP, BLASTN, and BLASTX algorithms (see Altschul et al. (1990) *J. Mol. Biol.* 215:403–410). Alignment is also often performed by inspection and manual alignment.

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman et al. (1970) *J. Mol. Biol.* 48:443. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

The invention is drawn to methods for creating or enhancing resistance in a plant to plant pests by modulating the activity of the Mlo3 gene in the plant. While the invention is not bound by any particular mechanism of action, it is believed that the methods of the invention will result in broad-based resistance in the modified plant. Accordingly, the methods are also useful in protecting plants against fungal pathogens, viruses, nematodes, insects and the like.

By "modulating activity" is intended that the expression of the Mlo3 gene is altered in some manner. Such modulation (increase or decrease) of expression results in enhanced resistance to pathogens. Generally, the methods of the invention will result in a decrease in the native protein or in protein activity. Thus, plants and plant cells are obtained having altered levels of MLO3 protein, preferably a decrease in protein levels. Such plants, plant cells and plant tissues are "modified" in that MLO3 protein levels are altered. As noted below, various methods are available for creating modified plants, plant cells and plant tissues including transformation and transfection leading to altered Mlo3 expression in the modified plant, plant cell or tissue.

The invention is drawn to compositions and methods for inducing resistance in a plant to plant pests. Accordingly, the compositions and methods are also useful in protecting plants against fungal pathogens, viruses, nematodes, insects and the like.

By "disease resistance" is intended that the plants avoid the disease symptoms that are the outcome of plant-pathogen interactions. That is, pathogens are prevented from causing plant diseases and the associated disease symptoms, or alternatively, the disease symptoms caused by the pathogen is minimized or lessened. The methods of the invention can be utilized to protect plants from disease, particularly those diseases that are caused by plant pathogens.

Pathogens of the invention include, but are not limited to, viruses or viroids, bacteria, insects, nematodes, fungi, and the like. Viruses include any plant virus, for example, tobacco or cucumber mosaic virus, ringspot virus, necrosis virus, maize dwarf mosaic virus, etc. Specific fungal and viral pathogens for the major crops include: Soybeans: *Phytophthora megasperma* fsp. *glycinea, Macrophomina phaseolina, Rhizoctonia solani, Sclerotinia sclerotiorum, Fusarium oxysporum, Diaporthephaseolorum* var. *sojae* (*Phomopsis sojae*), *Diaporthe phaseolorum* var. *caulivora, Sclerotium rolfsii, Cercospora kikuchii, Cercospora sojina, Peronospora manshurica, Colletotrichum dematium* (*Colletotichum truncatum*), *Corynespora cassiicola, Septoria glycines, Phyllosticta sojicola, Alternaria alternata, Pseudomonas syringae* p.v. *glycinea, Xanthomonas campestris* p.v. *phaseoli, Microsphaera difusa, Fusarium semitectum, Phialophora gregata,* Soybean mosaic virus, *Glomerella glycines,* Tobacco Ring spot virus, Tobacco Streak virus, *Phakopsora pachyrhizi, Pythium aphanidermatum, Pythium ultimum, Pythium debaryanum,* Tomato spotted wilt virus, *Heterodera glycines Fusarium*

*solani;* Canola: *Albugo candida, Alternaria brassicae, Leptosphaeria maculans, Rhizoctonia solani, Sclerotinia sclerotiorum, Mycosphaerella brassiccola, Pythium ultimum, Peronospora parasitica, Fusarium roseum, Alternaria alternata;* Alfalfa: *Clavibater michiganese* subsp. *insidiosum, Pythium ultimum, Pythium irregulare, Pythium splendens, Pythium debaryanum, Pythium aphanidermatum, Phytophthora megasperma, Peronospora trifoliorum, Phoma medicaginis* var. *medicaginis, Cercospora medicaginis, Pseudopeziza medicaginis, Leptotrochila medicaginis,* Fusarium, *Xanthomonas campestris* p.v. *alfalfae, Aphanomyces euteiches, Stemphylium herbarum, Stemphylium alfalfae;* Wheat: *Pseudomonas syringae* p.v. *atrofaciens, Urocystis agropyri, Xanthomonas campestris* p.v. *translucens, Pseudomonas syringae* p.v. *syringae, Alternaria alternata, Cladosporium herbarum, Fusarium graminearum, Fusarium avenaceum, Fusarium culmorum, Ustilago tritici, Ascochyta tritici, Cephalosporium gramineum, Collotetrichum graminicola, Erysiphe graminis* f.sp. *tritici, Puccinia graminis* f.sp. *tritici, Puccinia recondita* f.sp. *tritici, Puccinia striiformis, Pyrenophora tritici-repentis, Septoria nodorum, Septoria tritici, Septoria avenae, Pseudocercosporella herpotrichoides, Rhizoctonia solani, Rhizoctonia cerealis, Gaeumannomyces graminis* var. *tritici, Pythium aphanidermatum, Pythium arrhenomanes, Pythium ultimum, Bipolaris sorokiniana,* Barley Yellow Dwarf Virus, Brome Mosaic Virus, Soil Borne Wheat Mosaic Virus, Wheat Streak Mosaic Virus, Wheat Spindle Streak Virus, American Wheat Striate Virus, *Claviceps purpurea, Tilletia tritici, Tilletia laevis, Ustilago tritici, Tilletia indica, Rhizoctonia solani, Pythium arrhenomannes, Pythium gramicola, Pythium aphanidermatum,* High Plains Virus, European wheat striate virus; Sunflower: *Plasmophora halstedii, Sclerotinia sclerotiorum,* Aster Yellows, *Septoria helianthi, Phomopsis helianthi, Alternaria helianthi, Alternaria zinniae, Botrytis cinerea, Phoma macdonaldii, Macrophomina phaseolina, Erysiphe cichoracearum, Rhizopus oryzae, Rhizopus arrhizus, Rhizopus stolonifer, Puccinia helianthi, Verticillium dahliae, Erwinia carotovorum* pv. *carotovora, Cephalosporium acremonium, Phytophthora cryptogea, Albugo tragopogonis;* Corn: *Fusarium moniliforme* var. *subglutinans, Erwinia stewartii, Fusarium moniliforme, Gibberella zeae* (*Fusarium graminearum*), *Stenocarpella maydi* (*Diplodia maydis*), *Pythium irregulare, Pythium debaryanum, Pythium graminicola, Pythium splendens, Pythium ultimum, Pythium aphanidermatum, Aspergillusflavus, Bipolaris maydis* O,T (*Cochliobolus heterostrophus*), *Helminthosporium carbonum* I, II & III (*Cochliobolus carbonum*), *Exserohilum turcicum* I, II & III, *Helminthosporium pedicellatum, Physoderma maydis, Phyllosticta maydis, Kabatiella-maydis, Cercospora sorghi, Ustilago maydis, Puccinia sorghi, Puccinia polysora, Macrophomina phaseolina, Penicillium oxalicum, Nigrospora oryzae, Cladosporium herbarum, Curvularia lunata, Curvularia inaequalis, Curvulariapallescens, Clavibacter michiganense* subsp. *nebraskense, Trichoderma viride,* Maize Dwarf Mosaic Virus A & B, Wheat Streak Mosaic Virus, Maize Chlorotic Dwarf Virus, *Claviceps sorghi, Pseudonomas avenae, Erwinia chrysanthemi* pv. *zea, Erwinia carotovora, Corn stunt spiroplasma, Diplodia macrospora, Sclerophthora macrospora, Peronosclerospora sorghi, Peronosclerospora philippinensis, Peronosclerospora maydis, Peronosclerospora sacchari, Sphacelotheca reiliana, Physopella zeae, Cephalosporium maydis, Cephalosporium acremonium,* Maize Chlorotic Mottle Virus, High Plains Virus, Maize Mosaic Virus, Maize Rayado Fino Virus, Maize Streak Virus, Maize Stripe Virus, Maize Rough Dwarf Virus; Sorghum: *Exserohilum turcicum, Colletotrichum graminicola* (*Glomerella graminicola*), *Cercospora sorghi, Gloeocercospora sorghi, Ascochyta sorghina, Pseudomonas syringae* p.v. syringae, *Xanthomonas campestris* p.v. *holcicola, Pseudomonas andropogonis, Pucciniapurpurea, Macrophomina phaseolina, Perconia circinata, Fusarium moniliforme, Alternaria alternata, Bipolaris sorghicola, Helminthosporium sorghicola, Curvularia lunata, Phoma insidiosa, Pseudomonas avenae* (Pseudomonas alboprecipitans), *Ramulispora sorghi, Ramulispora sorghicola, Phyllachara sacchari, Sporisorium reilianum* (*Sphacelotheca reiliana*), *Sphacelotheca cruenta, Sporisorium sorghi,* Sugarcane mosaic H, Maize Dwarf Mosaic Virus A & B, *Claviceps sorghi, Rhizoctonia solani, Acremonium strictum, Sclerophthona macrospora, Peronosclerospora sorghi, Peronosclerospora philippinensis, Sclerospora graminicola, Fusarium graminearum, Fusarium oxysporum, Pythium arrhenomanes, Pythium graminicola,* etc.

Nematodes include parasitic nematodes such as root-knot, cyst, lesion, and renniform nematodes, etc.

Insect pests include insects selected from the orders Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera, etc., particularly Coleoptera and Lepidoptera. Insect pests of the invention for the major crops include: Maize: *Ostrinia nubilalis,* European corn borer; *Agrotis ipsilon,* black cutworm; *Helicoverpa zea,* corn earworm; *Spodopterafrugiperda,* fall armyworm; *Diatraea grandiosella,* southwestern corn borer; *Elasmopalpus lignosellus,* lesser cornstalk borer; *Diatraea saccharalis,* surgarcane borer; *Diabrotica virgifera,* western corn rootworm; *Diabrotica longicornis barberi,* northern corn rootworm; *Diabrotica undecimpunctata howardi,* southern corn rootworm; *Melanotus spp.,* wireworms; *Cyclocephala borealis,* northern masked chafer (white grub); *Cyclocephala immaculata,* southern masked chafer (white grub); *Popillia japonica,* Japanese beetle; *Chaetocnema pulicaria,* corn flea beetle; *Sphenophorus maidis,* maize billbug; *Rhopalosiphum maidis,* corn leaf aphid; *Anuraphis maidiradicis,* corn root aphid; *Blissus leucopterus leucopterus,* chinch bug; *Melanoplus femurrubrum,* redlegged grasshopper; *Melanoplus sanguinipes,* migratory grasshopper; *Hylemya platura,* seedcorn maggot; *Agromyza parvicornis,* corn blot leafminer; *Anaphothrips obscrurus,* grass thrips; *Solenopsis milesta,* thief ant; *Tetranychus urticae,* twospotted spider mite; Sorghum: *Chilo partellus,* sorghum borer: *Spodoptera frugiperda,* fall armyworm; *Helicoverpa zea,* corn earworm; *Elasmopalpus lignosellus,* lesser cornstalk borer; *Feltia subterranea,* granulate cutworm; *Phyllophaga crinita,* white grub; Eleodes, Conoderus, and Aeolus spp., wireworms; *Oulema melanopus,* cereal leaf beetle; *Chaetocnema pulicaria,* corn flea beetle; *Sphenophorus maidis,* maize billbug; *Rhopalosiphum maidis;* corn leaf aphid; *Sipha flava,* yellow sugarcane aphid; *Blissus leucopterus leucopterus,* chinch bug; *Contarinia sorghicola,* sorghum midge; *Tetranychus cinnabarinus,* carmine spider mite; *Tetranychus urticae,* twospotted spider mite; Wheat: *Pseudaletia unipunctata,* army worm; *Spodoptera frugiperda,* fall armyworm; *Elasmopalpus lignosellus,* lesser cornstalk borer; *Agrotis orthogonia*, western cutworm; *Elasmopalpus lignosellus,* lesser cornstalk borer; *Oulema melanopus,* cereal leaf beetle; *Hypera punctata,* clover leaf weevil; *Diabrotica undecimpunctata howardi,* southern corn rootworm; Russian wheat aphid; *Schizaphis graminum,* greenbug; *Macrosiphum avenae,* English grain aphid; *Melanoplus femurrubrum,* redlegged grasshopper; *Melanoplus diferentialis,* differential grasshopper; *Melanoplus sanguinipes,* migratory grasshopper; *Mayetiola destructor,* Hessian fly; *Sitodiplosis mosellana,* wheat midge; *Meromyza americana,* wheat stem maggot; *Hylemya coarctata,* wheat bulb fly; *Frankliniella fusca,* tobacco thrips; *Cephus cinctus,* wheat stem sawfly; *Aceria tulipae,* wheat curl mite; Sunflower: *Suleima helianthana,* sunflower bud moth; *Homoeosoma electellum,* sunflower moth; *zygogramma exclamationis,* sunflower beetle; *Bothyrus gibbosus,* carrot beetle; *Neolasioptera murtfeldtiana,* sunflower seed midge; Cotton: *Heliothis virescens,* cotton budworm; *Helicoverpa zea,* cotton bollworm; *Spodoptera exigua,* beet armyworm; *Pectinophora gossypiella,* pink bollworm, *Anthonomus grandis grandis,* boll weevil; *Aphis gossypii,* cotton aphid; *Pseudatomoscelis seriatus,* cotton fleahopper; *Trialeurodes abutilonea,* bandedwinged whitefly; *Lygus lineolaris,* tarnished plant bug; *Melanoplusfemurrubrum,* redlegged grasshopper; *Melanoplus differentialis,* differential grasshopper; *Thrips tabaci,* onion thrips; *Franklinkiella fusca,* tobacco thrips; *Tetranychus cinnabarinus,* carmine spider mite; *Tetranychus urticae,* twospotted spider mite; Rice: *Diatraea saccharalis,* sugarcane borer; *Spodoptera frugiperda,* fall armyworm; *Helicoverpa zea,* corn earworm; *Colaspis brunnea,* grape colaspis; *Lissorhoptrus oryzophilus,* rice water weevil; *Sitophilus oryzae,* rice weevil; *Nephotetfix nigropictus,* rice leafhopper; *Blissus leucopterus leucopterus,* chinch bug; *Acrosternum hilare,* green stink bug; Soybean: *Pseudoplusia includens,* soybean looper; *Anticarsia gemmatalis,* velvetbean caterpillar; *Plathypena scabra,* green cloverworm; *Ostrinia nubilalis,* European corn borer; *Agrotis ipsilon,* black cutworm; *Spodoptera exigua,* beet armyworm; *Heliothis virescens,* cotton budworm; *Helicoverpa zea,* cotton bollworm; *Epilachna varivestis,* Mexican bean beetle; *Myzus persicae,* green peach aphid; *Empoascafabae,* potato leafhopper; *Acrosternum hilare,* green stink bug; *Melanoplus femurrubrum,* redlegged grasshopper; *Melanoplus diferentialis,* differential grasshopper; *Hylemya platura,* seedcorn maggot; *Sericothrips variabilis,* soybean thrips; *Thrips tabaci,* onion thrips; *Tetranychus turkestani,* strawberry spider mite; *Tetranychus urticae,* twospotted spider mite; Barley: *Ostrinia nubilalis,* European corn borer; *Agrotis ipsilon,* black cutworm; *Schizaphis graminum,* greenbug; *Blissus leucopterus leucopterus,* chinch bug; *Acrosternum hilare,* green stink bug; *Euschistus servus,* brown stink bug; *Delia platura,* seedcorn maggot; *Mayetiola destructor,* Hessian fly; *Petrobia latens,* brown wheat mite; Oil Seed Rape: *Brevicoryne brassicae,* cabbage aphid; *Phyllotreta cruciferae,* Flea beetle; *Mamestra configurata,* Bertha armyworm; *Plutella xylostella,* Diamond-back moth; Delia ssp., Root maggots.

The present invention exploits the use of the Mlo3 gene. The Mlo3 sequence provided herein can be utilized to alter the expression of the native Mlo3 gene in plants. The mlo3 mutation confers recessive resistance to pathogens. Broad spectrum resistance in plants can be enhanced by a defective Mlo3 gene.

While the invention is not bound by any model, Mlo3 could have a negative control function in leaf cell death. In this model, Mlo3 would suppress a default cell suicide program in foliar tissue. Also, the MLO3 protein could have a specific negative regulatory function which works by down-regulating multiple disease-related functions. In this instance, spontaneous cell death in mlo3 mutant genotypes merely represents cell death because of accumulating activation of defense responses.

Several methods are available in the art for modulating the activity of the Mlo3 gene. Mlo3 antisense sequence can be expressed in the plant cell. Such sequence will function to decrease expression of the maize Mlo3 gene as well as Mlo3 genes in other plants where the Mlo3 sequences share sequence identity.

It is recognized that with these nucleotide sequences, antisense constructions, complementary to at least a portion of the messenger RNA (mRNA) for the Mlo3 sequence can be constructed. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, preferably 80%, more preferably 85% sequence similarity to the corresponding antisensed sequences may be used. Furthermore, portions of the antisense nucleotides may be used to disrupt the expression of the target gene. Generally, sequences of at least 50 nucleotides, 100 nucleotides, 200 nucleotides, or greater may be used.

The antisense construct may be proximal to the 5'-terminus or capping site, downstream from the capping site, between the capping site and the initiation codon and may cover all or a portion of the non-coding region. Additionally, the sequence may bridge the non-coding and coding region, be complementary to all or part of the coding region, to the 3'-terminus of the coding region, or complementary to the 3'-untranslated region of the mRNA.

It is recognized that the particular site to which the antisense sequence binds and the length of the antisense sequence will vary depending upon the degree of inhibition desired, the uniqueness of the sequence, the stability of the antisense sequence, and the like. See, for example, U.S. Pat. Nos. 5,453,566; 5,530,192; and 5,728,926; all of which are herein incorporated by reference.

The nucleotide sequences of the present invention may also be used in the sense orientation to suppress the expression of endogenous genes in plants. Methods for suppressing gene expression in plants using nucleotide sequences in the sense orientation are known in the art. The methods generally involve transforming plants with a DNA construct comprising a promoter that drives expression in a plant operably linked to at least a portion of the Mlo3 a nucleotide sequence. Typically, such a nucleotide sequence has substantial sequence identity to the sequence of the transcript of the endogenous gene, preferably greater than about 65% sequence identity, more preferably greater than about 85% sequence identity, most preferably greater than about 95% sequence identity. See, U.S. Pat. Nos. 5,283,184 and 5,034,323; herein incorporated by reference.

The individual Mlo3 gene can be rendered nonfunctional by mutagenesis. Such mutagenesis techniques include transposon disruption and recovery of such disruptions by reverse genetics approaches. Likewise, transformation-mediated mutagenesis may be utilized.

Disruption may be accomplished by transformation with gene replacement or gene truncation-disruption. See, for example, Bowen et al. (1995) *Mol. Gen. Gent.* 246:196–205; Walz et al. (1993) *Curr. Gent.* 25:421–427; Sweigard et al. (1992) *Mol. Gen. Gent.* 232:183–190; Hohn and Desjardins (1992) *Mol. Plant Microbe Interact* 5:249–256; Weber and Laitner (1994) *Curr. Gent.* 26:461–467; Templeton et al. (1994) *Gene* 142:141–146; Gorlach et al. (1998) *Appl. Environ. Microbiol.* 64:385–391; Schaeffer et al. (1994) *Appl. Environ. Microbiol.* 60:594–598; and the like, herein incorporated by reference. See also, Kempin et al. (1997) *Nature* 389:802–803 and Koncz et al. (1992) *Plant Mol. Biol.* 20:963–976.

Alternatively, the naturally occurring Mlo3 sequence may be modified by site-directed mutagenesis. Such methods may be utilized to induce specific alterations in targeted genes. One means for site-directed mutagenesis includes targeting modification or mutation of the Mlo3 sequence by homologous recombination. The method involves the use of RNA-DNA hybrid oligonucleotides. Such nucleotides exploit the natural recombinogenicity of RNA-DNA hybrids. The oligonucleotides are duplex oligonucleotides that share homology with the Mlo3 sequence. While any region of the Mlo3 sequence can be targeted, it may be preferable to target the 5' region of the Mlo3 sequence. See, for example, U.S. Pat. No, 5,565,350 that describes chimeric oligonucleotides useful for targeted gene correction for use in cultured mammalian cells; as well as U.S. provisional application Serial No. 60/065,628 drawn to gene manipulation in plant cells, herein incorporated by reference, Such methods can be used to alter or disrupt the ATG start codon for the gene.

Alternatively, the protein coding region of the Mlo3 gene can be altered in such a manner that the gene product or protein performs its function in a dominant negative manner resulting in a resistant phenotype. See, for example Krylov et al. (1997) *Proc. Natl. Acad. Sci. USA* 94:12274–12279.

Where the method of the invention relies upon the expression of an altered Mlo3 sequence or a Mlo3 antisense sequence in a plant, a number of promoters can be used. The promoters can be selected from constitutive and/or inducible promoters. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245–254; Uknes et al. (1992) *The Plant Cell* 4:645–656; and Van Loon (1985) *Plant Mol. Virol.* 4:111–116. See, also copending application entitled "Inducible Maize promoters", filed and herein incorporated by reference.

Of interest are promoters that are expressed locally at or near the site of pathogen infection. See, for example, Marineau et al. (1987) *Plant Mol Biol* 9:335–342; Matton et al. (1989) *Molecular Plant-Microbe Interactions* 2:325–33 1; Somsisch et al. (1986) *Proc. Natl. Acad. Sci. USA* 83:2427–2430; Somsisch et al. (1988) *Molecular and General Genetics* 2:93–98; and Yang, Y (1996) *Proc. Natl. Acad. Sci. USA* 93:14972–14977. See also, Chen et al. (1996) *Plant J.* 10:955–966; Zhang and Sing (1994) *Proc. Natl. Acad. Sci. USA* 91:2507–2511; Warner et al. (1993) *Plant J.* 3:191–201; Siebertz et al. (1989) *Plant Cell* 1:961–968; and the references cited therein. Of particular interest is the inducible promoter for the maize PRms gene, whose expression is induced by the pathogen *Fusarium moniliforme* (see, for example, Cordero et al. (1992) *Physiological and Molecular Plant Pathology* 41:189–200). Constitutive promoters include, for example, the core promoter of the Rsyn7 (copending application Ser. No. 08/661,601), the 35S promoter, the core 35S promoter, and the like. Other constitutive promoters include, for example, U.S. Pat. Nos. 5,608,149; 5,608,144; 5,604,121; 5,569,597; 5,466,785; 5,399,680; 5,268,463; 5,608,142. See also, copending application entitled "Constitutive Maize Promoters" Provisional Application Serial No. 60/076,075 filed Feb. 26, 1998, and herein incorporated by reference.

Tissue specific promoters include Yamamoto et al. (1997) *Plant J.* 12(2):255–265; Kawamata et al. (1997) *Plant Cell Physiol.* 38(7)792–803; Hansen et al. (1997) *Mol. Gen Genet.* 254(3):337–343; Russell et al. (1997) *Transgenic Res.* 6(2):157–168; Rinehart et al. (1996) *Plant Physiol.* 112(3):1331–1341; Van Camp et al. (1996) *Plant Physiol.* 112(2):525–535; Canevascini et al. (1996) *Plant Physiol.* 112(2):513–524; Yamamoto et al. (1994) *Plant Cell Physiol.* 35(5):773–778; Lam (1994) *Results Probl. Cell. Differ.* 20:181–196; Orozco et al. (1993) *Plant Mol. Biol.* 23(6):1129–1138; Matsuoka et al. (1993) *Proc. Natl. Acad. Sci. U.S.A.* 90(20):9586–9590; and Guevara-Garcia et al. (1993) *Plant J.* 4(3):495–505.

The methods of the invention can be used with other methods for increasing pathogen resistance in plants. See, for example, Cai et al. (1997) *Science* 275:832–834; Roberts and Gallum (1984) *J. Heredity* 75:147–148; Ryerson and Heath (1996) *Plant Cell* 8:393–402 and Dangl et al. (1996) *Plant Cell* 8:1793–1807.

Altered Mlo3 sequences or antisense Mlo3 sequences of the invention can be introduced into any plant. The sequence to be introduced may be used in expression cassettes for expression in any plant of interest where expression in the plant cell is necessary. In other instances, such as for recombination, oligonucleotides are synthesized, purified and introduced into the plant cell.

Where expression cassettes are needed, such expression cassettes will comprise a transcriptional initiation region linked to the coding sequence or antisense sequence of the nucleotide of interest. Such an expression cassette is provided with a plurality of restriction sites for insertion of the sequence to be under the transcriptional regulation of the regulatory regions. The expression cassefte may additionally contain selectable marker genes.

The transcriptional initiation region, the promoter, may be native or analogous or foreign or heterologous to the plant host. Additionally, the promoter may be the natural sequence or alternatively a synthetic sequence. By foreign is intended that the transcriptional initiation region is not found in the native plant into which the transcriptional initiation region is introduced. As used herein a chimeric gene comprises a coding sequence operably linked to a transcription initiation region that is heterologous to the coding sequence.

While it may be preferable to express the sequence using heterologous promoters, the native promoter sequences may be used, Such constructs would change the expression levels of the MLO3 protein in the plant or plant cell. Thus, the phenotype of the plant or plant cell is altered.

The transcriptional cassette will include in the 5'-3' direction of transcription, a transcriptional and translational initiation region, a DNA sequence of interest, and a transcriptional and translational termination region functional in plants. The termination region may be native with the transcriptional initiation region, may be native with the DNA sequence of interest, or may be derived from another source. Convenient termination regions are available from the Ti-plasmid of *A. tumefaciens,* such as the octopine synthase and nopaline synthase termination regions. See also, Guerineau etal. (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell.* 2:1261–1272; Munroe et al. (1990) *Gene* 91:151–158; Ballas et al. (1989) *Nucleic Acids Res.* 17:7891–7903; Joshi et al. (1987) *Nucleic Acid Res.* 15:9627–9639.

Nucleotide sequences of the invention are provided in expression cassettes for expression in the plant of interest. The cassette will include 5' and 3' regulatory sequences operably linked to the sequence of interest. The cassette may additionally contain at least one additional sequence to be cotransformed into the organism. Alternatively, the additional sequence(s) can be provided on another expression cassette.

Where appropriate, the gene(s) may be optimized for increased expression in the transformed plant. That is, the genes can be synthesized using plant-preferred codons for improved expression. See, for example, Campbell and Gowri (1990) *Plant Physiol.* 92:1–11 for a discussion of host-preferred codon usage. Methods are available in the art for synthesizing plant-preferred genes. See, for example, U.S. Pat. Nos. 5,380,831, 5,436,391, and Murray et al. (1989) Nucleic Acids Res. 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *PNAS USA* 86:6126–6130); potyvirus leaders, for example, TEV leader (Tobacco Etch Virus) (Allison et al. (1986); MDMV leader (Maize Dwarf Mosaic Virus): *Virology* 154:9–20), and human immunoglobulin heavy-chain binding protein (BiP), (Macejak et al. (1991) *Nature* 353:90–94); untranslated leader from the coat protein mRNA of alfalfa mosaic virus (AMV RNA 4) (Jobling et al. (1987) Nature 325:622–625); tobacco mosaic virus leader (TMV) (Gallie et al. (1989) in Molecular Biology of RNA, ed. Cech (Liss, New York), pp. 237–256); and maize chlorotic mottle virus leader (MCMV) (Lommel et al. (1991) *Virology* 81:382–385). See also, Della-Cioppa et al. (1987) *Plant Physiol.* 84:965–968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Towards this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g. transitions and transversions, may be involved.

The sequences of the present invention can be used to transform or transfect any plant. In this manner, genetically modified plants, plant cells, plant tissue, seed, and the like can be obtained. Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320–334), electroporation (Riggs et al. (1986) *Proc. Natl. Acad. Sci. USA* 83:5602–5606, Agrobacterium-mediated transformation (Townsend et al., U.S. Pat No. 5,563,055), direct gene transfer (Paszkowski et al. (1984) *EMBO J.* 3:2717–2722), and ballistic particle acceleration (see, for example, Sanford et al., U.S. Pat. No. 4,945,050; Tomes et al. (1995) "Direct DNA Transfer into Intact Plant Cells via Microprojectile Bombardment," in *Plant Cell, Tissue, and Organ Culture: Fundamental Methods,* ed. Gamborg and Phillips (Springer-Verlag, Berlin); and McCabe et al. (1988) *Biotechnology* 6:923–926). Also see Weissinger et al. (1988) *Ann. Rev. Genet.* 22:421–477; Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Finer and McMullen (1991) *In Vitro Cell Dev. Biol.* 27P: 175–182 (soybean); Singh et al. (1998) *Theor. Appl. Genet.* 96:319–324 (soybean); Datta et al. (1990) *Biotechnology* 8:736–740 (rice); Klein et al. (1988) *Proc. Natl. Acad. Sci. USA* 85:4305–4309 (maize); Klein et al. (1988) *Biotechnology* 6:559–563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods,* ed. Gamborg (Springer-Verlag, Berlin) (maize); Klein et al. (1988) *Plant Physiol.* 91:440–444 (maize); Fromm et al. (1990) *Biotechnology* 8:833–839 (maize); Hooykaas-Van Slogteren et al. (1984) *Nature* (London) 311:763–764; Bowen et al., U.S. Pat. No. 5,736,369 (cereals); Bytebier et al. (1987) *Proc. Natl. Acad. Sci. USA* 84:5345–5349 (Liliaceae); De Wet et al. (1985) in *The Experimental Manipulation of Ovule Tissues,* ed. Chapman et al. (Longman, New York), pp. 197–209 (pollen); Kaeppler et al. (1990) *Plant Cell Reports* 9:415–418 and Kaeppler et al. (1992) *Theor. Appl. Genet.* 84:560–566 (whisker-mediated transformation); D'Halluin et al. (1992) *Plant Cell* 4:1495–1505 (electroporation); Li et al. (1993) *Plant Cell Reports* 12:250–255 and Christou and Ford (1995) *Annals of Botany* 75:407–413 (rice); Osjoda et al. (1996) *Nature Biotechnology* 14:745–750 (maize via *Agrobacterium tumefaciens*); all of which are herein incorporated by reference.

The modified plant may be grown into plants in accordance with conventional ways. See, for example, McCormick et al. (1986) *Plant Cell. Reports,* 5:81–84. These plants may then be grown, and either pollinated with the same transformed strain or different strains, and the resulting hybrid having the desired phenotypic characteristic identified. Two or more generations may be grown to ensure that the subject phenotypic characteristic is stably maintained and inherited and then seeds harvested to ensure the desired phenotype or other property has been achieved.

The Mlo3 sequence of the invention is also useful as a molecular marker. Such a marker is useful in breeding programs, particularly those aimed at improving disease resistance. The maize Mlo3 sequence has been mapped to a chromosome location and this position relates to known disease resistance loci.

The present invention provides a method of genotyping a plant comprising a polynucleotide of the present invention. Preferably, the plant is a monocot, such as maize or sorghum. Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance. See, e.g., *Plant Molecular Biology: A Laboratory Manual,* Chapter 7, Clark, Ed., Springer-Verlag, Berlin (1997). For molecular marker methods, see generally, The DNA Revolution by Andrew H. Paterson (1996) (Chapter 2) in: Genome Mapping in Plants (ed. Andrew H. Paterson) by Academic Press/R. G. Landis Company, Austin, Tex., pp. 7–21.

The particular method of genotyping in the present invention may employ any number of molecular marker analytic techniques such as, but not limited to, restriction fragment length polymorphisms (RFLPs). RFLPs are the product of allelic differences between DNA restriction fragments caused by nucleotide sequence variability. As is well known to those of skill in the art, RFLPs are typically detected by extraction of genomic DNA and digestion with a restriction enzyme. Generally, the resulting fragments are separated according to size and hybridized with a probe; single copy probes are preferred. Restriction fragments from homologous chromosomes are revealed. Differences in fragment size among alleles represent an RFLP. Thus, the present invention further provides a means to follow segregation of a gene or nucleic acid of the present invention as well as chromosomal sequences genetically linked to the Mlo3 gene or nucleic acids using such techniques as RFLP analysis. Linked chromosomal sequences are within 50 centiMorgans (Cm), often within 40 or 30 Cm, preferably within 20 or 10 Cm, more preferably within 5, 3, 2, or 1 Cm of a gene.

In the present invention, the nucleic acid probes employed for molecular marker mapping of plant nuclear genomes selectively hybridize, under selective hybridization conditions, to a gene encoding a polynucleotide of the present invention. In preferred embodiments, the probes are selected from a polynucleotide of the present invention. Typically, these probes are cDNA probes or PstI genomic clones. The length of the probes is discussed in greater detail, supra, but are typically at least 15 bases in length, more preferably at least 20, 25, 30, 35, 40, or 50 bases in length. Generally, however, the probes are less than about 1 kilobase in length. Preferably, the probes are single copy probes that hybridize to a unique locus in a haploid chromosome complement. Some exemplary restriction enzymes employed in RFLP mapping are EcoRI, EcoRv, and SstI. As used herein the term "restriction enzyme" includes reference to a composition that recognizes and, alone or in conjunction with another composition, cleaves at a specific nucleotide sequence.

The method of detecting an RFLP comprises the steps of (a) digesting genomic DNA of a plant with a restriction enzyme; (b) hybridizing a nucleic acid probe, under selective hybridization conditions, to a sequence of a polynucleotide of the present of said genomic DNA; (c) detecting therefrom a RFLP. Other methods of differentiating polymorphic (allelic) variants of polynucleotides of the present invention can be had by utilizing molecular marker techniques well known to those of skill in the art including such techniques as: 1) single-stranded conformation analysis (SSCP); 2) denaturing gradient gel electrophoresis (DGGE), 3) Rnase protection assays; 4) allele-specific oligonucleotides (ASOs); 5) the use of proteins which recognize nucleotide mismatches, such as the *E. coli* mutS protein; and 6) allele-specific PCR. Other approaches based on the detection of mismatches between the two complementary DNA strands include clamped denaturing gel electrophoresis (CDGE); heteroduplex analysis (HA); and chemical mismatch cleavage (CMC). Exemplary polymorphic variants are provided in Table I, supra. Thus, the present invention further provides a method of genotyping comprising the steps of contacting, under stringent hybridization conditions, a sample suspected of comprising a polynucleotide of the present invention with a nucleic acid probe. Generally, the sample is a plant sample; preferably, a sample suspected of comprising a maize polynucleotide of the present invention (e.g., gene, mRNA). The nucleic acid probe selectively hybridizes, under stringent conditions, to a subsequence of a polynucleotide of the present invention comprising a polymorphic marker. Selective hybridization of the nucleic acid probe to the polymorphic marker nucleic acid sequence yields a hybridization complex. Detection of the hybridization complex indicates the presence of that polymorphic marker in the sample. In preferred embodiments, the nucleic acid probe comprises a polynucleotide of the present invention.

The following examples are offered by way of illustration and not by way of limitation.

EXPERIMENTAL

Mlo3 Sequences

The Mlo3 sequence has been identified. The nucleotide sequence (SEQ ID NO: 1) and amino acid sequence (SEQ ID NO: 2) are provided. DNA sequence analysis was performed according to Sambrook et al. (1989) *Mol. Cloning: A Laboratory Manual,* 2nd ed. (Cold Spring Harbor Laboratory Press, Plainview, N.Y. The maize Mlo3 homologue/orthologue cDNA sequence was identified from mRNA isolated from various maize tissues and used to make cDNAs that are then cloned into vectors, usually pSPORT1. These cDNA libraries are EST sequenced via standard dye-fluorescence labeling and ABI machine electrophoresis and image capture. The Mlo3 homologue was identified by its blast score identity to the barley HvMLO1 published sequence. This maize clone, in particular the longest member of each contig or gene, was obtained and additional sequencing was done using oligonucleotide primers designed to internal portions of the cDNA and dye-fluorescence labeling and ABI machine electrophoresis and image capture. The complete edited sequence was assembled and analyzed.

The sequences from maize show sequence similarity to the published barley Mlo sequence. FIG. 1 provides a sequence alignment for the maize Mlo3 homologue with the barley Mlo sequence designated as HvMlo1.

The ZmMLO3 gene was mapped by RFLP analysis using Southern blots of genomic DNA isolated from F2 and F3 and F4 segregating maize populations. The DNA was isolated using a modified CTAB adapted from the CERES RFLP Lab Manuel based on the Saghai-Mahoof procedure (Saghai-Mahoof et al. (1984) *Proc. Natl. Acad. Sci. USA* 81:8014–8018). Genomic DNA was cut with four restriction enzymes BamHI, EcoRI, EcoRV, and HindIII and run (5 μg/lane) on 0.8% TAE agarose gels for 800 volt-hours. The gels were Southern blot transferred to Hybond-N membrane (Amersham Life Science), baked and UV-crosslinked. The ZmMLO3 cDNA inserts were liberated from its vector by cleaving with two restriction enzymes, usually SalI and NotI, and the insert was purified from agarose gels following electrophoresis. The clone was random prime labeled with $^{32}P$-dCTP using the RTS (Gibco BRL) labeling kit. The cDNA insert was used to probe parental screening blots to identify a mapping population with a RFLP polymorphism. Once a polymorphism was identified, the inserts were used to probe mapping blots containing DNA from segregating individuals. The map position was determined using MAPMAKER/EXP 3.0 (Lander et al (1987) *Genomics*

1:174–181) by scoring 86 segregating progeny as homozygous parent A, as homozygous parent B, or as heterozygous. The map position was assigned to an existing core RFLP map of either of the following three populations: ALEB9 (240 individuals) DRAG2 (283 individuals) or MARS (1075 individuals). Table 1 shows the association of maize Mlo3 gene and disease related loci and QTLS.

TABLE 1

Association of Maize MLO3 and Disease Related Loci and QTLs

| Maize MLO Homologue | | Nearby Disease Resistance Loci or QTLs | |
|---|---|---|---|
| ZmMlo3 | 2.04 | 2.04 | Lesion Mimic Les1 |
| | | 2.04 | Lesion Mimic Les 15 |
| | | 2.04/5 | Gray Leaf Spot QTL |

TABLE 2

Mutator Insertion Mutants of ZmMLO3 (TUSC)

| ZmMLO3 | |
|---|---|
| PV03 95A1 | *C. carbonum* susceptibility (segregating as recessive) |
| PV03 112A4 | *C. carbonum* susceptibility (segregating as recessive) |
| PV03 158F2 | *C. carbonum* susceptibility (segregating) |
| BT94 83G8 | *C. carbonum* susceptibility (segregating as recessive); independent of *C. heterostrophus* intermediate resistance (segregating as recessive) |
| BT94 83E1 | *C. carbonum* susceptibility (segregating as recessive) (sib) |

5'-AGAGAAGCCAACGCCA(AT)CGCCTC(CT)ATTTCGTC-3' (SEQ ID NO: 6). Seven positive "hits" to ZmMLO3 were identified. Twenty F2 seeds for each of the hits were planted in the greenhouse and screened as follows. Seeds were planted in trays, containing 2-inch wells for each seed, in Strong-Lite (circleR) Universal Mix potting soil (Universal Mix, Pine Bluff, Ark., U.S.A.) and grown in a greenhouse (16 hour day, 20.6–34.8° C., 50% average RH, 560–620 microEinsteins, of light both sun and halogen lamps, averaging 25 heat units per day. Plants were grown for 14–18 days until the V5 stage (ca. 25 cm height) and inoculated with spores of *Cochliobolus heterostrophus* (Drechs.) Dreshs. Race 0, also known as *Bipolaris maydis* (Southern Leaf Blight) and *Cochliobolus carbonum* R. R Nelson, also known as *Bipolaris zeicola* (Helminthosporium Leaf Spot). For general leaf inoculation, spore suspensions of $4\times10^4$ per ml of 0.02% Tween-20 were sprayed as an aerosol on the leaves. Approximately 0.5 ml were applied per leaf late in the afternoon. The plants were then immediately covered with a plastic tent and kept at R.T. in order to enhance humidity and spore germination. The plastic tent was removed early in the morning, and the plants were returned to the greenhouse for the duration of the experiment, usually three days. Susceptibility to *Cochliobolus carbonum* was determined by either increased size or number of lesions. Resistance to *Cochliobolus heterostrophus* was determined by either reduced size or number of lesions. Lesion mimics were also investigated; these mutations form spontaneous lesions in the absence of pathogen attach. Other phenotypes affecting growth and development were also noted.

TABLE 3

| Gene Mapping Information | Gene Complexity on Southern blot | Chromosome location (bin) | Chromosome location (arm) | Nearby Public Marker | Distance from Public Marker | Distance | LOD Score | RFLP Restriction Enzyme | Mapping Population | Mapping Parents (Public Names) |
|---|---|---|---|---|---|---|---|---|---|---|
| ZmMlo3 | 1 | 2.04 | 2S | Umc131 | 15.6 (up) | 15.6 | 19 | HindIII | MARS | N46/RO3 |

Example 1: Transformation and Regeneration of Transgenic Plants
Immature maize embryos from greenhouse donor plants are bombarded with a plasmid containing the ZmMLO3 antisense sequence operably linked to the ubiquitin promoter (FIG. 2). This plasmid also contains the selectable marker gene PAT (Wohlleben et al. (1988) Gene 70:25–37) that confers resistance to the herbicide Bialophos. Transformation is performed as follows. All media recipes are in the Appendix.

The Trait Utility System for corn (TUSC) system was utilized to generate transposon mutants in the Mlo3 sequence in maize. The combination of transposon mutagenesis via Mutator and PCR-based selection of target-specific Mu insertions makes up the TUSC system. See, for example, Benson et al. (1995) *Plant Cell.* 7:75–84; Mena et al. (1996) *Science* 274:1537–1540; U.S. patent application Ser. Nos. 08/835,638 and 08/262,056; all of which are herein incorporated by reference. Table 2 shows Mutator insertion mutants of ZmMlo3.

Oligonucleotide primers based on Mlo3 maize sequence were designed and paired with Mu TIR primer in PCR reactions. The products of the screening process identify individuals in the collection having Mu elements inserted into the Mlo3 sequence.

The gene-specific primers used for TUSC of ZmMLO3 are: 19011, 5'-CTCTGCTGCTTCTGATTGGGACGAATCT-3' (SEQ ID NO:4); and 19013, 5'-CAGGGTCGTAATAGTGGCACAAGAGG-3' (SEQ ID NO: 5). For TUSC of the Mlo3 gene the mutator-element specific primer used was: 9242,

Example 1

Transformation and Regeneration of Transgenic Plants

Immature maize embryos from greehouse donor plants are bombarded with a plasmid containing the ZmML03 antisense sequence operably linked to the ubiquitin promoter (FIG. 2). This plasmid also contains the selectable marker gene PAT (Wohllenben et al. (1988) Gene 70:25–37) that confers resistance to the herbicide Bialophos. Transformation is performed as follows. All media recipes are in the Appendix.

Preparation of Target Tissue

The ears are surface sterilized in 30% Chlorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid vector comprising the PAT selectable marker and the ZmMlo3 antisense sequence operably linked to a the ubiquitin is made and precipitated onto 1.1 μm (average diameter) tungsten pellets using a $CaCl_2$ precipitation procedure as follows:

100 μl prepared tungsten particles in water

10 μl (1 μg) DNA in TrisEDTA buffer (1 μg total)

100 μl 2.5 M $CaCl_2$

10 μl 0.1 M spermidine

Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.

Particle Gun Treatment

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2–4 weeks), well-developed somatic embryos are transferred to medium for germination and transferred to the lighted culture room. Approximately 7–10 days later, developing plantlets are transferred to 272V hormone-free medium in tubes for 7–10 days until plantlets are well established. Plants are then transferred to inserts in flats (equivalent to 2.5" pot) containing potting soil and grown for 1 week in a growth chamber, subsequently grown an additional 1–2 weeks in the greenhouse, then transferred to classic 600 pots (1.6 gallon) and grown to maturity. Plants are monitored and scored for enhanced disease resistance as a result of antisense disruption of ZmMlo3 function.

APPENDIX

272 V

| Ingredient | Amount | Unit |
|---|---|---|
| D-I $H_2O$ | 950.000 | Ml |
| MS Salts (GIBCO 11117-074) | 4.300 | G |
| Myo-Inositol | 0.100 | G |
| MS Vitamins Stock Solution ## | 5.000 | Ml |
| Sucrose | 40.000 | G |
| Bacto-Agar @ | 6.000 | G |

Directions:
@ = Add after bringing up to volume
Dissolve ingredients in polished D-I $H_2O$ in sequence
Adjust to pH 5.6
Bring up to volume with polished D-I $H_2O$ after adjusting pH
Sterilize and cool to 60° C.

-continued

APPENDIX

272 V

| Ingredient | Amount | Unit |
|---|---|---|

## = Dissolve 0.100 g of Nicotinic Acid; 0.020 g of Thiamine.HCL; 0.100 g of Pyridoxine.HCL; and 0.400 g of Glycine in 875.00 ml of polished D-I $H_2O$ in sequence. Bring up to volume with polished D-I $H_2O$. Make in 400 ml portions. Thiamine.HCL & Pyridoxine.HCL are in Dark Desiccator. Store for one month, unless contamination or precipitation occurs, then make fresh stock.

Total Volume (L) = 1.00

288 J

| Ingredient | Amount | Unit |
|---|---|---|
| D-I $H_2O$ | 950.000 | Ml |
| MS Salts | 4.300 | g |
| Myo-Inositol | 0.100 | g |
| MS Vitamins Stock Solution ## | 5.000 | ml |
| Zeatin .5 mg/ml | 1.000 | ml |
| Sucrose | 60.000 | g |
| Gelrite @ | 3.000 | g |
| Indoleacetic Acid 0.5 mg/ml # | 2.000 | ml |
| 0.1 mM Abscisic Acid | 1.000 | ml |
| Bialaphos 1 mg/ml # | 3.000 | ml |

Directions:

@ = Add after bringing up to volume

Dissolve ingredients in polished D-I $H_2O$ in sequence

Adjust to pH 5.6

Bring up to volume with polished D-I $H_2O$ after adjusting pH

Sterilize and cool to 60° C.

Add 3.5 g/L of Gelrite for cell biology.

## = Dissolve 0.100 g of Nicotinic Acid; 0.020 g of Thiamine.HCL; 0.100 g of Pyridoxine.HCL; and 0.400 g of Glycine in 875.00 ml of polished D-I $H_2O$ in sequence. Bring up to volume with polished D-I $H_2O$. Make in 400 ml portions. Thiamine.HCL & Pyridoxine.HCL are in Dark Desiccator. Store for one month, unless contamination or precipitation occurs, then make fresh stock.

Total Volume (L) = 1.00

560 R

| Ingredient | Amount | Unit |
|---|---|---|
| D-I Water, Filtered | 950.000 | ml |
| CHU (N6) Basal Salts (SIGMA C-1416) | 4.000 | g |
| Eriksson's Vitamin Mix (1000X SIGMA-1511) | 1.000 | ml |
| Thiamine.HCL 0.4 mg/ml | 1.250 | ml |
| Sucrose | 30.000 | g |
| 2,4-D 0.5 mg/ml | 4.000 | ml |
| Gelrite @ | 3.000 | g |
| Silver Nitrate 2mg/ml # | 0.425 | ml |
| Bialaphos 1 mg/ml # | 3.000 | ml |

Directions:
@ = Add after bringing up to volume
# = Add after sterilizing and cooling to temp.

-continued

| 560 R | | |
|---|---|---|
| Ingredient | Amount | Unit |
| Dissolve ingredients in D-I $H_2O$ in sequence | | |
| Adjust to pH 5.8 with KOH | | |
| Bring up to volume with D-I $H_2O$ | | |
| Sterilize and cool to room temp. | | |
| Total Volume (L) = 1.00 | | |

| 560 Y | | |
|---|---|---|
| Ingredient | Amount | Unit |
| D-I Water, Filtered | 950.000 | ml |
| CHU (N6) Basal Salts (SIGMA C-1416) | 4.000 | g |
| Eriksson's Vitamin Mix (1000X SIGMA-1511) | 1.000 | ml |
| Thiamine.HCL 0.4 mg/ml | 1.250 | ml |
| Sucrose | 120.000 | g |
| 2,4-D 0.5 mg/ml | 2.000 | ml |
| L-Proline | 2.880 | g |
| Gelrite @ | 2.000 | g |
| Silver Nitrate 2 mg/ml # | 4.250 | ml |

Directions:
@ = Add after bringing up to volume
# = Add after sterilizing and cooling to temp.

-continued

| 560 Y | | |
|---|---|---|
| Ingredient | Amount | Unit |
| Dissolve ingredients in D-I $H_2O$ in sequence | | |
| Adjust to pH 5.8 with KOH | | |
| Bring up to volume with D-I $H_2O$ | | |
| Sterilize and cool to room temp. | | |
| **Autoclave less time because of increased sucrose** | | |
| Total Volume (L) = 1.00 | | |

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. An isolated MLO3 protein, said protein comprising the amino acid sequence set forth in SEQ ID NO: 2.

2. An isolated protein comprising at least 80% amino acid sequence identity to the amino acid sequence set forth in SEQ ID NO: 2, wherein said protein is capable of enhancing the resistance of a plant to at least one pathogen.

3. An isolated protein comprising at least 85% amino acid sequence identity to the amino acid sequence set forth in SEQ ID NO: 2, wherein said protein is capable of enhancing the resistance of a plant to at least one pathogen.

4. The isolated protein of claim 3, wherein said protein comprises at least 90% amino acid sequence identity to the amino acid sequence set forth in SEQ ID NO: 2.

5. The isolated protein of claim 4, wherein said protein comprises at least 95% amino acid sequence identity to the amino acid sequence set forth in SEQ ID NO: 2.

* * * * *

UNITED STATES PATENT AND TRADEMARK OFFICE

CERTIFICATE OF CORRECTION

PATENT NO. : 6,403,768 B1
DATED : June 11, 2002
INVENTOR(S) : Simmons et al.

It is certified that error appears in the above-identified patent and that said Letters Patent is hereby corrected as shown below:

Title page,
Item [75], Inventors: the second inventor's name, "Mia" should read -- Miao --.

Signed and Sealed this

Fourth Day of March, 2003

JAMES E. ROGAN
*Director of the United States Patent and Trademark Office*

SEQUENCE LISTING

```
<160> NUMBER OF SEQ ID NOS: 6

<210> SEQ ID NO 1
<211> LENGTH: 1869
<212> TYPE: DNA
<213> ORGANISM: Zea mays
<220> FEATURE:
<223> OTHER INFORMATION: Mlo3

<400> SEQUENCE: 1

gaagagttca gctaccctac catccacact ttattcatct cagggcagta g ccagtagct     60

agctgtagag ggagttatcg gccatgtcgg aggaggcgac gctggaggac a cgcctacgt    120

ggatcgtggc gtccgtgtgc tccgtcatcg tcctcatctc cttcgtcttc g agcgcgcgc    180

tccaccacct cggcaaggca ctggagcgcc ggaggaagac cctgtacgag g cgctgctaa    240

agctcaaaga agagctcatg ctgctgggct tcgtctcgct gctcctcgtc g tctcccagg    300

acttgataca gaagatctgc atcgacgaca gcctcatgga gcactggatg c cgtgccggg    360

gtgcgagcgc caccgcctcg gctcattacg gtgtctcctc ctcctcctcc t cctccgcgg    420

tcggtggcgg gaggaggatg ctcaaaggcg gcggggcagc tttcgggcac t gttcaagca    480

agggaaaagt cccgttgcta tcacttcacg ccttggagca ggtacacatt t tcatcttcg    540

tcctagctat cacgcaagtc gttctcagcg tcgccaccgt cctcctggga c ttctgcaga    600

tgcggatatg gatgcactgg gagaacacca ttcagcaaga gggcagctct g ctcccaaga    660

tgatcgcccg tgtgcagaaa atcaggttca tccaggaccg gtgtaagggg t acgagaagg    720

ccgcctgggt tataatatgg ctgcgttctt tcttcaaaca gttctacgga t cagtgtcca    780

acgacgacta cattgcgatg agactcggtt tcgtcatgga gcactttagg g ggcacccca    840

agttcaactt ttacgactac atgatcaaag ctctcgagaa agatttcaag c gagtagtta    900
```

-continued gtataaaatg gtattactgg atttttgtga tgatctttct gctgctcaat g tcaccgggt 960 ggcactccta cttctggatc tcattagttc cactggctct gctgcttctg a ttgggacga 1020 agctggagca catcataaac aggctggcct acgaggtggc ctcgaagcac g ccgccgggc 1080 aaggcgaagg gggcatcgtg gtgagccctt cggacgagct gttctggttc c gcagcccac 1140 ggctggtgct cgtgctcatc cacttcatcc tgttccagaa cgcgttcgag t tcgcgtatt 1200 tcttctggac actggcgatg ttcggcgcca actcctgcat catggacagt c taggataca 1260 gcgtctcgcg aatcatcata tgcgtcgtcg tccaggtgct ctgcagctac a gcacactcc 1320 cgctctacgc catcgtgtcc catatgggga gttcgttcaa gagcgctgtg t tcgtggacg 1380 acgtcgccga caatctcaga gggtgggccg acggcgcccg gaggcgcgtg c ggagatctg 1440 ccacgggtgt cgacgccagt tgcctgggta cgccggcggc ggcgggacgg g gctgggaag 1500 gcgccgccgg ctggagattg attgccggga ggccgagccg cccaactcag c agcctcgga 1560 gcatctcctt ctgagttctg tctagtttct gaagaaggaa tcgaaagccg c gcaatctgc 1620 agcacgcgta tgctgtcgct gcccgtcttc atttgggtat tattgggttt g agttgacac 1680 tgaccaactg ccgaattttg cggaaacttt tatggtcatg cctcttgtgc c actattacg 1740 accgtggcgg tgagcacgga gtgtaataga gtagtaaaga tatgtagctc g catatatat 1800 atatatactg tacctccgcc cgtgatgcta gcagtagcag cggcggatgg g gctctagcg 1860 gcattgttg 1869

<210> SEQ ID NO 2
<211> LENGTH: 496
<212> TYPE: PRT
<213> ORGANISM: Zea mays
<220> FEATURE:
<223> OTHER INFORMATION: Mlo3

<400> SEQUENCE: 2

Met Ser Glu Glu Ala Thr Leu Glu Asp Thr P ro Thr Trp Ile Val Ala
1 5 10 15

Ser Val Cys Ser Val Ile Val Leu Ile Ser P he Val Phe Glu Arg Ala
20 25 30

Leu His His Leu Gly Lys Ala Leu Glu Arg A rg Arg Lys Thr Leu Tyr
35 40 45

Glu Ala Leu Leu Lys Leu Lys Glu Glu Leu M et Leu Leu Gly Phe Val
50 55 60

Ser Leu Leu Leu Val Val Ser Gln Asp Leu I le Gln Lys Ile Cys Ile
65 70 75 80

Asp Asp Ser Leu Met Glu His Trp Met Pro C ys Arg Gly Ala Ser Ala
85 90 95

Thr Ala Ser Ala His Tyr Gly Val Ser Ser S er Ser Ser Ser Ser Ala
100 105 110

Val Gly Gly Gly Arg Arg Met Leu Lys Gly G ly Gly Ala Ala Phe Gly
115 120 125

His Cys Ser Ser Lys Gly Lys Val Pro Leu L eu Ser Leu His Ala Leu
130 135 140

Glu Gln Val His Ile Phe Ile Phe Val Leu A la Ile Thr Gln Val Val
145 150 155 160

Leu Ser Val Ala Thr Val Leu Leu Gly Leu L eu Gln Met Arg Ile Trp
165 170 175

Met His Trp Glu Asn Thr Ile Gln Gln Glu G ly Ser Ser Ala Pro Lys

-continued 180 185 190

Met Ile Ala Arg Val Gln Lys Ile Arg Phe I le Gln Asp Arg Cys Lys
195 200 205

Gly Tyr Glu Lys Ala Ala Trp Val Ile Ile T rp Leu Arg Ser Phe Phe
210 215 220

Lys Gln Phe Tyr Gly Ser Val Ser Asn Asp A sp Tyr Ile Ala Met Arg
225 230 235 240

Leu Gly Phe Val Met Glu His Phe Arg Gly H is Pro Lys Phe Asn Phe
245 250 255

Tyr Asp Tyr Met Ile Lys Ala Leu Glu Lys A sp Phe Lys Arg Val Val
260 265 270

Ser Ile Lys Trp Tyr Tyr Trp Ile Phe Val M et Ile Phe Leu Leu Leu
275 280 285

Asn Val Thr Gly Trp His Ser Tyr Phe Trp I le Ser Leu Val Pro Leu
290 295 300

Ala Leu Leu Leu Leu Ile Gly Thr Lys Leu G lu His Ile Ile Asn Arg
305 310 315 320

Leu Ala Tyr Glu Val Ala Ser Lys His Ala A la Gly Gln Gly Glu Gly
325 330 335

Gly Ile Val Val Ser Pro Ser Asp Glu Leu P he Trp Phe Arg Ser Pro
340 345 350

Arg Leu Val Leu Val Leu Ile His Phe Ile L eu Phe Gln Asn Ala Phe
355 360 365

Glu Phe Ala Tyr Phe Phe Trp Thr Leu Ala M et Phe Gly Ala Asn Ser
370 375 380

Cys Ile Met Asp Ser Leu Gly Tyr Ser Val S er Arg Ile Ile Ile Cys
385 390 395 400

Val Val Val Gln Val Leu Cys Ser Tyr Ser T hr Leu Pro Leu Tyr Ala
405 410 415

Ile Val Ser His Met Gly Ser Ser Phe Lys S er Ala Val Phe Val Asp
420 425 430

Asp Val Ala Asp Asn Leu Arg Gly Trp Ala A sp Gly Ala Arg Arg Arg
435 440 445

Val Arg Arg Ser Ala Thr Gly Val Asp Ala S er Cys Leu Gly Thr Pro
450 455 460

Ala Ala Ala Gly Arg Gly Trp Glu Gly Ala A la Gly Trp Arg Leu Ile
465 470 475 480

Ala Gly Arg Pro Ser Arg Pro Thr Gln Gln P ro Arg Ser Ile Ser Phe
485 490 495

<210> SEQ ID NO 3
<211> LENGTH: 533
<212> TYPE: PRT
<213> ORGANISM: Hordeum vulgare

<400> SEQUENCE: 3

Met Ser Asp Lys Lys Gly Val Pro Ala Arg G lu Leu Pro Glu Thr Pro
1 5 10 15

Ser Trp Ala Val Ala Val Val Phe Ala Ala M et Val Leu Val Ser Val
20 25 30

Leu Met Glu His Gly Leu His Lys Leu Gly H is Trp Phe Gln His Arg
35 40 45

His Lys Lys Ala Leu Trp Glu Ala Leu Glu L ys Met Lys Ala Glu Leu
50 55 60

-continued

```
Met Leu Val Gly Phe Ile Ser Leu Leu Leu I le Val Thr Gln Asp Pro
 65                  70                  75                  80

Ile Ile Ala Lys Ile Cys Ile Ser Glu Asp A la Ala Asp Val Met Trp
                 85                  90                  95

Pro Cys Lys Arg Gly Thr Glu Gly Arg Lys P ro Ser Lys Tyr Val Asp
            100                 105                 110

Tyr Cys Pro Glu Gly Lys Val Ala Leu Met S er Thr Gly Ser Leu His
        115                 120                 125

Gln Leu His Val Phe Ile Phe Val Leu Ala V al Phe His Val Thr Tyr
    130                 135                 140

Ser Val Ile Thr Ile Ala Leu Ser Arg Leu L ys Met Arg Thr Trp Lys
145                 150                 155                 160

Lys Trp Glu Thr Glu Thr Thr Ser Leu Glu T yr Gln Phe Ala Asn Asp
                165                 170                 175

Pro Ala Arg Phe Arg Phe Thr His Gln Thr S er Phe Val Lys Arg His
            180                 185                 190

Leu Gly Leu Ser Ser Thr Pro Gly Ile Arg T rp Val Val Ala Phe Phe
        195                 200                 205

Arg Gln Phe Phe Arg Ser Val Thr Lys Val A sp Tyr Leu Thr Leu Arg
    210                 215                 220

Ala Gly Phe Ile Asn Ala His Leu Ser Gln A sn Ser Lys Phe Asp Phe
225                 230                 235                 240

His Lys Tyr Ile Lys Arg Ser Met Glu Asp A sp Phe Lys Val Val Val
                245                 250                 255

Gly Ile Ser Leu Pro Leu Trp Gly Val Ala I le Leu Thr Leu Phe Leu
            260                 265                 270

Asp Ile Asn Gly Val Gly Thr Leu Ile Trp I le Ser Phe Ile Pro Leu
        275                 280                 285

Val Ile Leu Leu Cys Val Gly Thr Lys Leu G lu Met Ile Ile Met Glu
    290                 295                 300

Met Ala Leu Glu Ile Gln Asp Arg Ala Ser V al Ile Lys Gly Ala Pro
305                 310                 315                 320

Val Val Glu Pro Ser Asn Lys Phe Phe Trp P he His Arg Pro Asp Trp
                325                 330                 335

Val Leu Phe Phe Ile His Leu Thr Leu Phe G ln Asn Ala Phe Gln Met
            340                 345                 350

Ala His Phe Val Trp Thr Val Ala Thr Pro G ly Leu Lys Lys Cys Tyr
        355                 360                 365

His Thr Gln Ile Gly Leu Ser Ile Met Lys V al Val Val Gly Leu Ala
    370                 375                 380

Leu Gln Phe Leu Cys Ser Tyr Met Thr Phe P ro Leu Tyr Ala Leu Val
385                 390                 395                 400

Thr Gln Met Gly Ser Asn Met Lys Arg Ser I le Phe Asp Glu Gln Thr
                405                 410                 415

Ser Lys Ala Leu Thr Asn Trp Arg Asn Thr A la Lys Glu Lys Lys Lys
            420                 425                 430

Val Arg Asp Thr Asp Met Leu Met Ala Gln M et Ile Gly Asp Ala Thr
        435                 440                 445

Pro Ser Arg Gly Ser Ser Pro Met Pro Ser A rg Gly Ser Ser Pro Val
    450                 455                 460

His Leu Leu His Lys Gly Met Gly Arg Ser A sp Asp Pro Gln Ser Ala
465                 470                 475                 480

Pro Thr Ser Pro Arg Thr Gln Gln Glu Ala A rg Asp Met Tyr Pro Val
```

-continued

```
            485                 490                 495

Val Val Ala His Pro Val His Arg Leu Asn P ro Asn Asp Arg Arg Arg
            500                 505                 510

Ser Ala Ser Ser Ser Ala Leu Glu Ala Asp I le Pro Ser Ala Asp Phe
        515                 520                 525

Ser Phe Ser Gln Gly
    530


<210> SEQ ID NO 4
<211> LENGTH: 28
<212> TYPE: DNA
<213> ORGANISM: Artificial Sequence
<220> FEATURE:
<223> OTHER INFORMATION: Description of Artificial  Sequence:
      oligonucleotide primer

<400> SEQUENCE: 4

ctctgctgct tctgattggg acgaatct                                         28


<210> SEQ ID NO 5
<211> LENGTH: 26
<212> TYPE: DNA
<213> ORGANISM: Artificial Sequence
<220> FEATURE:
<223> OTHER INFORMATION: Description of Artificial  Sequence:
      oligonucleotide primer

<400> SEQUENCE: 5

cagggtcgta atagtggcac aagagg                                           26


<210> SEQ ID NO 6
<211> LENGTH: 32
<212> TYPE: DNA
<213> ORGANISM: Artificial Sequence
<220> FEATURE:
<223> OTHER INFORMATION: Description of Artificial  Sequence:
      oligonucleotide primer

<400> SEQUENCE: 6

agagaagcca acgccawcgc ctcyatttcg tc                                    32
```